(12) United States Patent
Suzuki et al.

(10) Patent No.: US 11,496,695 B2
(45) Date of Patent: Nov. 8, 2022

(54) ENDOSCOPE APPARATUS AND METHOD OF PROCESSING RADIAL IMAGES

(71) Applicant: OLYMPUS CORPORATION, Tokyo (JP)

(72) Inventors: Takeo Suzuki, Hachioji (JP); Mariko Otagiri, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/206,728

(22) Filed: Mar. 19, 2021

(65) Prior Publication Data

US 2021/0211586 A1 Jul. 8, 2021

Related U.S. Application Data

(63) Continuation of application No. PCT/JP2018/035635, filed on Sep. 26, 2018.

(51) Int. Cl.
*H04N 5/262* (2006.01)
*G06T 7/246* (2017.01)
(Continued)

(52) U.S. Cl.
CPC ....... *H04N 5/2628* (2013.01); *A61B 1/00006* (2013.01); *A61B 1/00045* (2013.01);
(Continued)

(58) Field of Classification Search
CPC ............. H04N 5/2628; H04N 5/23293; H04N 2005/2255; H04N 5/2254; H04N 5/232;
(Continued)

(56) References Cited

U.S. PATENT DOCUMENTS

2002/0006000 A1* 1/2002 Kumata ............... H04N 5/2254
359/857
2008/0247061 A1* 10/2008 Simkulet ................ G02B 13/06
359/857
(Continued)

FOREIGN PATENT DOCUMENTS

JP 2007307090 A 11/2007
JP 2010099178 A 5/2010
(Continued)

OTHER PUBLICATIONS

International Search Report dated Nov. 27, 2018 received in PCT/JP2018/035635.

*Primary Examiner* — Richard T Torrente
(74) *Attorney, Agent, or Firm* — Scully, Scott, Murphy & Presser, P.C.

(57) ABSTRACT

An endoscope apparatus includes a processor configured to carry out a reversal process on a side image of a subject picked up with an image pickup device, the reversal process reversing an order of a plurality of pixels located in the side image and arranged from a predetermined position in a radial direction, and cause a display apparatus to display a front image and the side image of the subject picked up with the image pickup device as a display image. The processor adjusts the timing at which the front image is displayed in such a way that the front image acquired simultaneously with the side image is displayed at a timing that accords with the timing at which the side image having undergone the reversal process is displayed on the display apparatus.

14 Claims, 12 Drawing Sheets

(51) Int. Cl.
*A61B 1/00* (2006.01)
*A61B 1/05* (2006.01)
*H04N 5/232* (2006.01)
*G06T 3/00* (2006.01)
*H04N 5/225* (2006.01)

(52) U.S. Cl.
CPC .............. *A61B 1/05* (2013.01); *G06T 3/0018* (2013.01); *G06T 3/0093* (2013.01); *G06T 7/248* (2017.01); *H04N 5/23293* (2013.01); *G06T 2207/10068* (2013.01); *G06T 2207/20021* (2013.01); *G06T 2207/20212* (2013.01); *H04N 2005/2255* (2013.01)

(58) Field of Classification Search
CPC ... A61B 1/00006; A61B 1/00045; A61B 1/05; A61B 1/00009; A61B 1/00096; A61B 1/00177; A61B 1/00181; G06T 7/248; G06T 2207/10068; G06T 2207/20021; G06T 2207/20212
See application file for complete search history.

(56) References Cited

U.S. PATENT DOCUMENTS

2010/0272318 A1   10/2010  Cabiri et al.
2020/0233233 A1*  7/2020  Lo .......................... H04N 21/41

FOREIGN PATENT DOCUMENTS

| | | |
|---|---|---|
| JP | 2011056106 A | 3/2011 |
| JP | 2011062328 A | 3/2011 |
| JP | 4779120 B2 | 9/2011 |
| JP | 4982358 B2 | 7/2012 |
| JP | 2012137665 A | 7/2012 |
| WO | 2006120690 A2 | 11/2006 |
| WO | 2015122354 A1 | 8/2015 |
| WO | 2015198981 A1 | 12/2015 |

* cited by examiner

ENDOSCOPE APPARATUS AND METHOD OF PROCESSING RADIAL IMAGES

CROSS REFERENCE TO RELATED APPLICATION

This application is a continuation application of PCT/JP2018/035635 filed on Sep. 26, 2018, the entire contents of which are incorporated herein by this reference.

BACKGROUND OF THE INVENTION

1. Field of the Invention

The present invention relates to an endoscope apparatus, an endoscopic image processing apparatus, and a method for operating the endoscopic image processing apparatus.

2. Description of the Related Art

An endoscope is widely used in medical and industrial fields. In an endoscope, an optical image of a subject incident on an observation window provided at a distal end section of an elongated insertion section is photoelectrically converted, and the resultant image is displayed on a display apparatus. For example, in the medical field, a surgeon can perform, for example, endoscopy on a patient while viewing an endoscopic image displayed on the display apparatus.

Some endoscopes have a wide field of view. For example, Japanese Patent Application Laid-Open Publication No. 2010-99178 proposes an endoscope apparatus capable of observing a front portion and a side-rear portion. A side-rear image is acquired, for example, by using an attachment including an annular convex mirror, and an endoscopic image including a front image and the side-rear image is displayed on the display apparatus.

When an endoscopic image including such a front image and a side image or a side-rear image is displayed on the display apparatus, the side image or the like is generated based on light reflected off the annular convex mirror, so that the annular side image or the like is a reversed version of an image of the subject actually viewed through the observation window.

When such a reversed annular side image or side-rear image and a non-reversed front image are simultaneously displayed, it is difficult for the surgeon or the like to intuitively understand, for example, the position of a diseased site.

Japanese Patent Application Laid-Open Publication No. 2010-99178 described above discloses a technology for reversing the order of arranged pixels of a side-rear image in such a way that inner pixels of the annular side-rear image (that is, central pixels) are displayed on an outer side and outer pixels of the annular side-rear image are displayed on an inner side to allow the surgeon or the like to intuitively understand, for example, the position of a diseased site.

SUMMARY OF THE INVENTION

An endoscope apparatus according to an aspect of the present invention includes an insertion section configured to be inserted into a subject, a first optical system configured to acquire an image of a first subject in front of the insertion section, a second optical system configured to reflect an odd number of times an image of a second subject in a lateral direction of the insertion section and acquire the reflected second subject image, an image pickup device configured to pick up the first subject image and the second subject image acquired by the first optical system and the second optical system, and a processor configured to carry out a reversal process on the second subject image picked up with the image pickup device, the reversal process reversing an order of a plurality of pixels located in the second subject image and arranged from a predetermined position in a radial direction, and cause a display apparatus to display the first subject image and the second subject image having undergone the reversal process as a display image. The processor is configured to adjust a timing at which at least the first subject image is displayed in such a way that the first subject image acquired simultaneously with the second subject image is displayed at a timing that accords with a timing at which the second subject image having undergone the reversal process is displayed on the display apparatus.

An endoscopic image processing apparatus according to another aspect of the present invention includes is an endoscopic image processing apparatus configured to be connected to an endoscope including an insertion section, a first optical system configured to acquire an image of a first subject in front of the insertion section, a second optical system configured to reflect an odd number of times an image of a second subject in a lateral direction of the insertion section and acquire the reflected second subject image, and an image pickup device configured to pick up the first subject image and the second subject image acquired by the first optical system and the second optical system, the endoscopic image processing apparatus including a processor including hardware. The processor carries out a reversal process on the second subject image picked up with the image pickup device, the reversal process reversing an order of a plurality of pixels located in the second subject image and arranged from a predetermined position in a radial direction, and outputs an image signal that causes a display apparatus to display the first subject image and the second subject image having undergone the reversal process as a display image, and the processor adjusts a timing at which at least the first subject image is displayed in such a way that the first subject image acquired simultaneously with the second subject image is displayed at a timing that accords with a timing at which the second subject image having undergone the reversal process is displayed on the display apparatus.

A method for operating an endoscopic image processing apparatus according to another aspect of the present invention is a method for operating an endoscopic image processing apparatus including a processor and connected to an endoscope including a first optical system configured to acquire a first subject image, a second optical system configured to reflect an odd number of times a second subject image in a lateral direction of the first subject image and acquire the reflected second subject image, and an image pickup device configured to pick up the first subject image and the second subject image. The processor carries out a reversal process on the second subject image, the reversal process reversing an order of a plurality of pixels located in the second subject image and arranged from a predetermined position in a radial direction, and outputs an image signal that causes a display apparatus to display the first subject image and the second subject image having undergone the reversal process as a display image, and the processor adjusts a timing at which at least the first subject image is displayed in such a way that the first subject image acquired simultaneously with the second subject image is displayed at a timing that accords with a timing at which the second subject image having undergone the reversal process is displayed on the display apparatus.

BRIEF DESCRIPTION OF THE DRAWINGS

FIG. 6 is a timing chart showing a procedure of image processing performed by the video processor according to the embodiment of the present invention;

FIG. 14 is a timing chart showing a procedure of image processing performed by the video processor according to Modification 3 of the embodiment of the present invention.

DETAILED DESCRIPTION OF THE PREFERRED EMBODIMENT

The present invention will be described below with reference to an embodiment.

Figure 1:
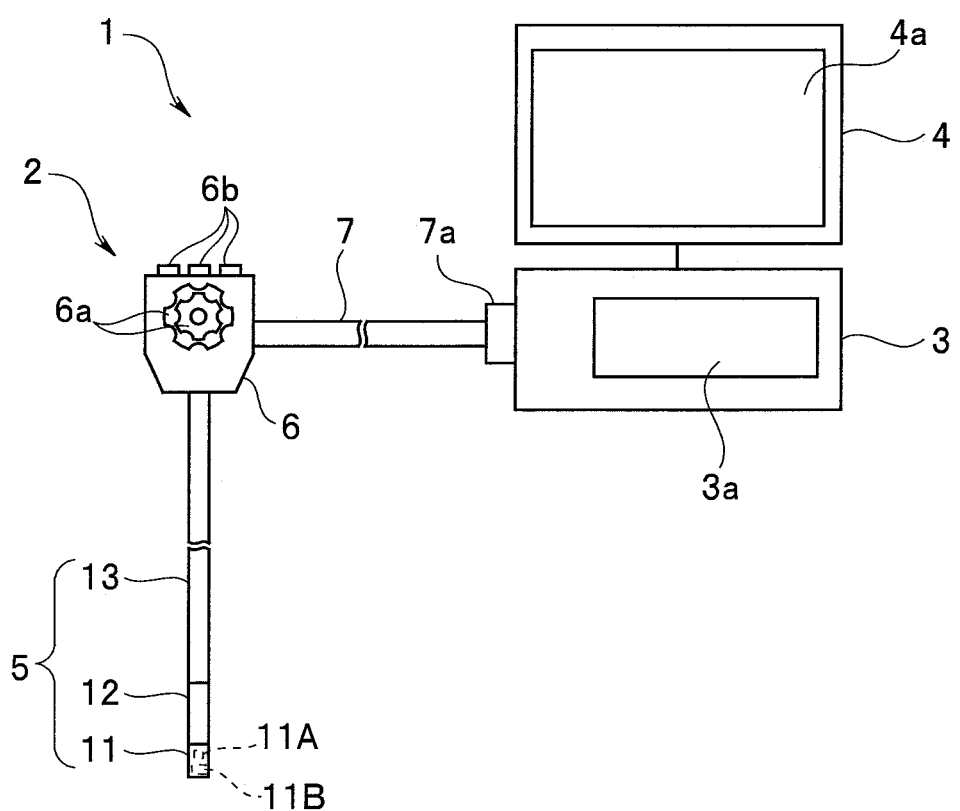
FIG. 1 is a configuration diagram of an endoscope apparatus according to an embodiment of the present invention.

FIG. 1 is a configuration diagram of an endoscope apparatus according to the embodiment of the present invention. The endoscope apparatus 1 includes an endoscope 2, a video processor 3, and a display apparatus 4. The endoscope 2 is a flexible endoscope and includes an elongated insertion section 5, an operation unit 6, to which a proximal end section of the insertion section 5 is connected, and a universal cable 7, which extends from the operation unit 6. Note that the endoscope 2 may be a rigid endoscope instead of a flexible endoscope.

The insertion section 5, which is inserted into a subject, includes a distal end section 11, a bending section 12, and a flexible tube section 13 sequentially arranged from the distal end. An image pickup unit 11A and an objective optical system 11B are incorporated in the distal end section 11.

Although not shown in FIG. 1, the distal end section 11 is provided with an observation window and an illumination window. The image pickup unit 11A is disposed on the optical axis of the objective optical system 11B provided behind the observation window. An illumination unit is disposed in the distal end section 11 in a position behind the illumination window via an illumination optical system. The illumination unit is, for example, a light emitting device, such as a light emitting diode.

The bending section 12 has a bending mechanism which is formed of a plurality of bending pieces and in which front ends of a plurality of bending wires are fixed to a front end bending piece.

The flexible tube section 13 is formed of a laminate of a flexible portion, a braid, and an outer skin resin arranged from inside. The flexible portion is a spiral tube as a flexible member having a shape of a spirally wound flat plate. The braid is a metallic network tube. The outer skin resin is formed around the outer circumferential portion of the braid such that part of the outer skin resin enters gaps between metal strands of the braid. The flexible tube section 13 is therefore rigid and flexible to some extent.

The operation unit 6 is provided with two disc-shaped pivotal motion knobs 6a configured to bend the bending section 12 and a plurality of operation buttons 6b configured to perform a variety of types of electrical operation. The bending section 12 can be bent in upward/downward and rightward leftward directions by pivotal motion operation of the two pivotal motion knobs 6a.

A connector 7a is provided at a distal end section of the universal cable 7, and the video processor 3 is connected to the connector 7a. The video processor 3 is an endoscopic image processing apparatus that accommodates, for example, a control circuit configured to control the image pickup unit 11A and an image generating/processing engine.

The video processor 3 includes an operation panel 3a. The operation panel 3a is, for example, a liquid crystal display apparatus with a touch panel apparatus. A surgeon or the like can operate a variety of buttons displayed on the operation panel 3a to input execution of a desired function to the video processor 3.

The display apparatus 4 is, for example, a liquid crystal display apparatus including a display screen 4a and displays, for example, an endoscopic image and a menu screen for a variety of types of operation.

Figure 2:
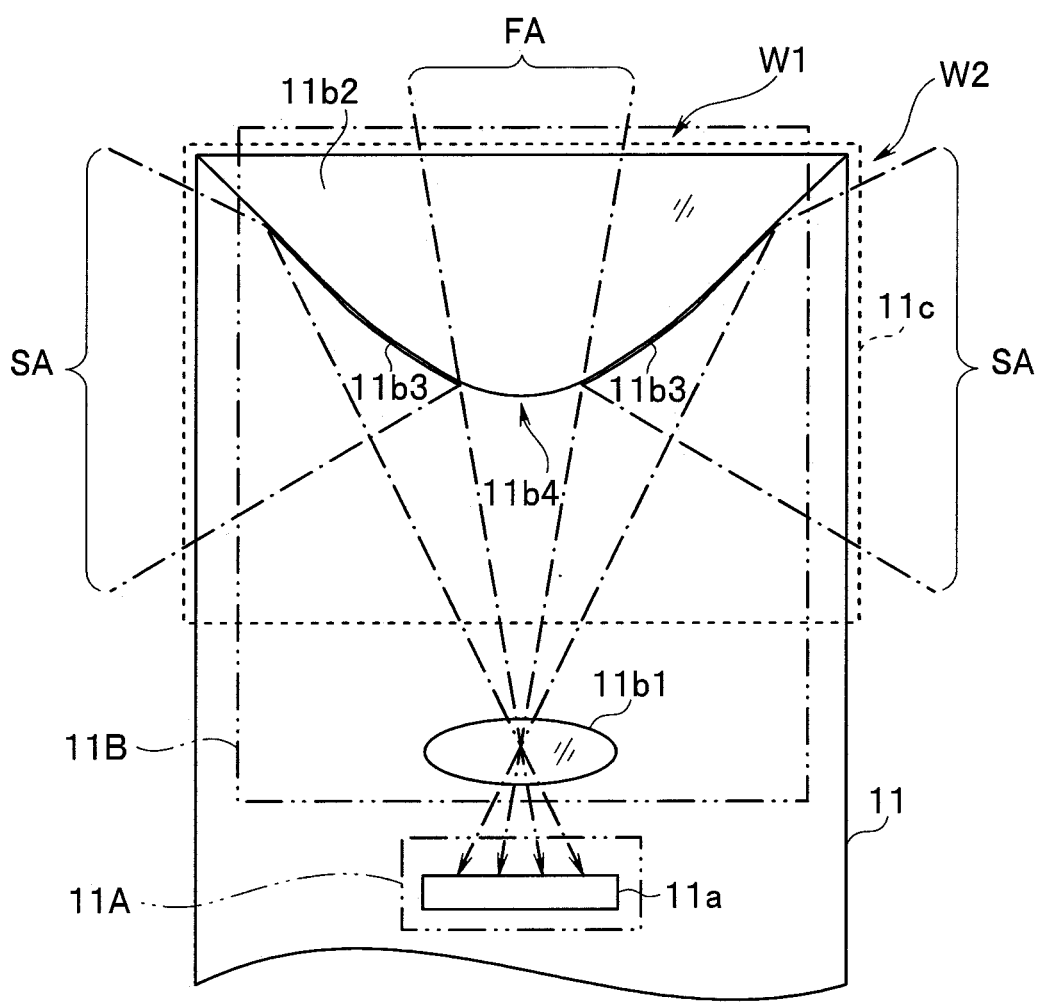
FIG. 2 is a configuration diagram of an image pickup unit and an objective optical system in a distal end section of an insertion section according to the embodiment of the present invention.

FIG. 2 is a configuration diagram of the image pickup unit 11A and the objective optical system 11B in the distal end section 11 of the insertion section 5. An image pickup device 11a as the image pickup unit 11A is disposed in the distal end section 11. The image pickup device 11a is an image sensor, such as a CCD and a CMOS device. The objective optical system 11B includes lenses 11b1 and 11b2 and an annular mirror section 11b3 formed on a surface of the lens 11b2.

The mirror section 11b3 is a convex mirror that convexly protrudes in a proximal end direction of the distal end section 11 that is a direction opposite to a distal end direction of the distal end section 11. The mirror section 11b3 has, for example, a hyperboloid or conical reflection surface. The mirror section 11*b*3 has a reflection surface formed by coating the convex outer surface of the lens 11*b*2, which is a planoconvex lens, for example, with evaporated aluminum.

When the distal end section 11 is viewed from the distal end direction, the lens 11*b*2 is disposed in the distal end section 11 such that a lens central section 11*h*4 of the lens 11*b*2, which is a section where no reflection surface of the mirror section 11*b*3 is formed, faces a central portion of an image pickup surface of the image pickup device 11*a*. The lens 11*b*1 is disposed between the mirror section 11*b*3 and the image pickup device 11*a*.

Light from a region in front of the distal end section 11 passes through the lens central section 11*b*4, passes through the lens 11*b*1, and is brought into focus on the image pickup surface of the image pickup device 11*a*. In other words, light from a front region FA in front of the distal end section 11 passes through the lenses 11*b*1 and 11*b*2 and converges onto the image pickup surface of the image pickup device 11*a* in FIG. 2.

Light from a lateral direction of the distal end section 11 is reflected off the mirror section 11*b*3, passes through the lens 11*b*1, and is brought into focus on the image pickup surface of the image pickup device 11*a*. In other words, light from a side region SA in the lateral direction of the distal end section 11 passes through the lens 11*b*1 and impinges on the image pickup device 11*a* in FIG. 2.

A first observation window W1 for the front region FA is disposed in a front-side distal end surface of the distal end section 11, and a second observation window W2 for the side region SA is disposed in an outer circumferential surface of the distal end section 11.

The lens 11*b*2 and the mirror section 11*b*3 are incorporated in the distal end section 11 in the description, but note that a section 11*c* including the lens 11*b*2 and the mirror section 11*b*3 in a distal end side portion of the distal end section 11 may be configured as an adaptor attachable to and detachable from the distal end section 11, as indicated by a dotted line in FIG. 2.

As described above, the light having passed through the lens central section 11*b*4 of the lens 11*b*2 passes through the lens 11*b*1 and is brought into focus on the image pickup surface of the image pickup device 11*a*. The lenses 11*b*1 and 11*b*2 therefore form an optical system configured to acquire an image of the subject in front of the distal end section 11 of the insertion section 5.

The light reflected off the annular mirror section 11*b*3 passes through the lens 11*b*1 and is brought into focus on the image pickup surface of the image pickup device 11*a*. The light reflected off the subject and traveling from a circumferential direction of the distal end section 11, which is the lateral direction of the distal end section 11 is reflected off the mirror section 11*b*3 once and directed toward the lens 11*b*1. In other words, the mirror section 11*b*3 in FIG. 2 reflects the subject image from the side of the distal end section 11 and directs the light toward the image pickup device 11*a* to via the lens 11*b*1.

The mirror section 11*b*3 and the lens 11*b*1 therefore form an optical system configured to reflect once and acquire the subject image from the side of the distal end section 11 of the insertion section 5. The image pickup unit 11A picks up two subject images acquired by the optical system formed of the lenses 11*b*1 and 11*b*2 and the optical system formed of the mirror section 11*b*3 and the lens 11*b*1.

Note that the optical system configured to reflect once the light from the subject may, for example, be an image pickup optical system disclosed in Japanese Patent No. 4,982,358.

In the present description, the mirror section 11*b*3 reflects once the light from the side and directs the light toward the lens 11*b*. The mirror section 11*b*3, which reflects the light once, may be replaced with a mirror configured to reflect the light from the side an odd number of times, such as three times, and directs the light toward the lens 11*b*.

Figure 3:
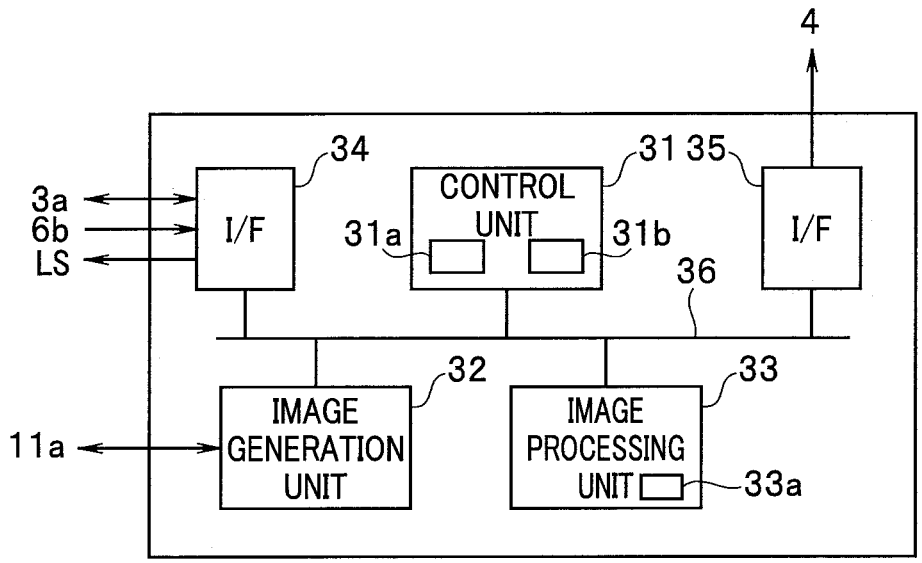
FIG. 3 is a block diagram showing the configuration of the video processor according to the embodiment of the present invention.

FIG. 3 is a block diagram showing the configuration of the video processor 3. Note that FIG. 3 only shows components relating to the present invention and does not show elements relating to other configurations, such as a light source for illumination light and recording apparatuses, for example, for image recording.

The video processor 3, which is an endoscopic image processing apparatus, includes a control unit 31, an image generation unit 32, an image processing unit 33, and interfaces 34 and 35. The control unit 31, the image generation unit 32, the image processing unit 33, and the interfaces 34 and 35 are connected to one another via a bus 36.

The control unit 31 includes a processor 31*a* including a hardware circuit, such as a central processing unit (CPU), and a memory 31*b*, such as a ROM. The ROM stores a variety of programs configured to achieve a variety of functions of the endoscope apparatus 1. A user, such as a surgeon, can operate the operation panel 3*a* or the variety of operation buttons 6*b* to issue a variety of commands to the endoscope apparatus 1. The variety of commands are received via the interface 34, and the processor 31*a* reads a program according to a received command from the ROM and executes the program.

The image generation unit 32 is a circuit configured to drive the image pickup device 11*a* and generate an image signal from an image pickup signal from the image pickup device 11*a*.

The image processing unit 33 cuts a front image and a side image from an image generated by the image generation unit 32 and generates a display image to be displayed on the display apparatus 4 under the control of the control unit 31. The image processing unit 33 includes a memory 33*a*, which stores, for example, the cut front image and side image, a reversed image that will be described later, and the generated display image.

The control unit 31 controls action of the image processing unit 33 in such a way that the image processing unit 33 acts in accordance with an action mode. The image processing unit 33 carries out a process according to an action instruction from the control unit 31. The image processing unit 33 can perform various types of image processing.

The control unit 31 outputs the image signal representing the display image generated by the image processing unit 33 to the display apparatus 4 via the interface 35. The interface 34 is an interface circuit configured to input and output signals from and to the operation panel 3*a*, the variety of operation buttons 6*b*, and other components.

The interface 34 also outputs an illumination drive signal LS to the illumination unit of the endoscope 2. The interface 35 is an interface circuit configured to output the display signal to the display apparatus 4.

Figure 4:
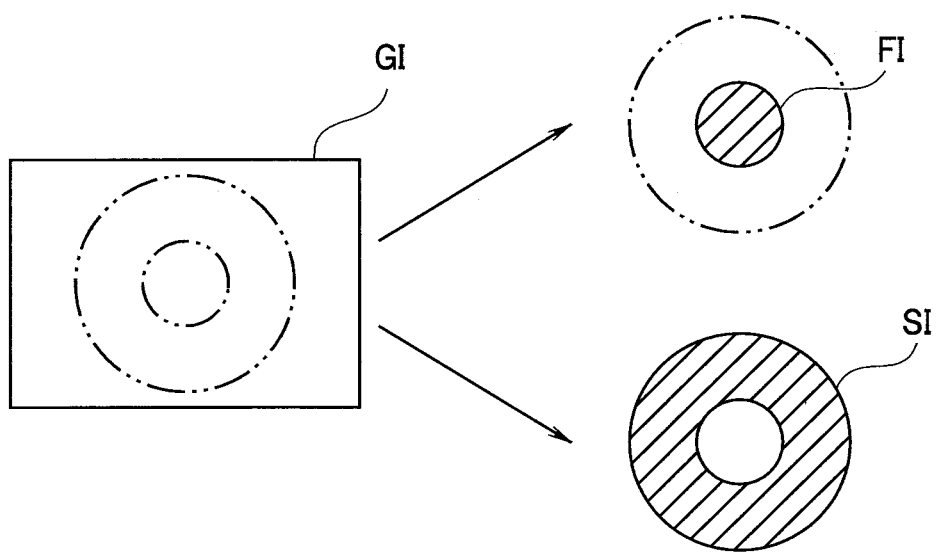
FIG. 4 describes operation of cutting a front image and a side image from an acquired image generated by an image generation unit according to the embodiment of the present invention.

A description will next be made of operation of cutting a front image and a side image in the image processing unit 33. FIG. 4 describes the operation of cutting a front image and a side image from an acquired image generated by the image generation unit 32.

The image pickup device 11*a* outputs an image pickup signal in accordance with a drive signal. The image pickup signal is supplied to the video processor 3 via a signal line inserted through the endoscope 2. The image pickup signal from the image pickup device 11a is inputted to the video processor 3 via the interface 34.

The image generation unit 32 acquires the image pickup signal via the interface 34 under the control of the control unit 31. The image generation unit 32 generates an image signal from the acquired image pickup signal. The image signal is a frame image.

The image pickup device 11a performs photoelectric conversion of the light from an object to generate the image pickup signal. When a frame rate is, for example, 1/30 (seconds), the image generation unit 32 generates the image signal every 1/30 seconds. In FIG. 4, an acquired image GI represents an image generated by the image generation unit 32 based on the image pickup signal from the image pickup device 11a. The image pickup surface of the image pickup device 11a has a rectangular shape, and the acquired image GI therefore has a rectangular shape.

Since the objective optical system 11B and the image pickup unit 11A are fixed and disposed in the distal end section 11, the image processing unit 33 generates a front image FI and a side image SI by cutting a predetermined region from the acquired image GI generated by the image generation unit 32, as shown in FIG. 4. The objective optical system 11B described above generates the front image FI and the side image SI such that the front image FI is a circular image formed in a roughly central portion of the acquired image GI, and the side image SI is an annular image formed in an outer circumferential portion of the front image FI.

Note that the side image SI of the endoscopic image in FIG. 4 may be a partially annular image instead of a fully annular image.

The circular front image FI and the annular side image SI are combined with each other and displayed on the display screen 4a of the display apparatus 4. The image generation, cutting, combination, and other processes described above are performed by the processor 31a of the control unit 31.

Effects

Action of the video processor 3 will next be described. While the video processor 3 can perform a variety of functions, only a function of displaying the front image FI and the side image SI relating to the present claimed invention will be described below.

Figure 5:
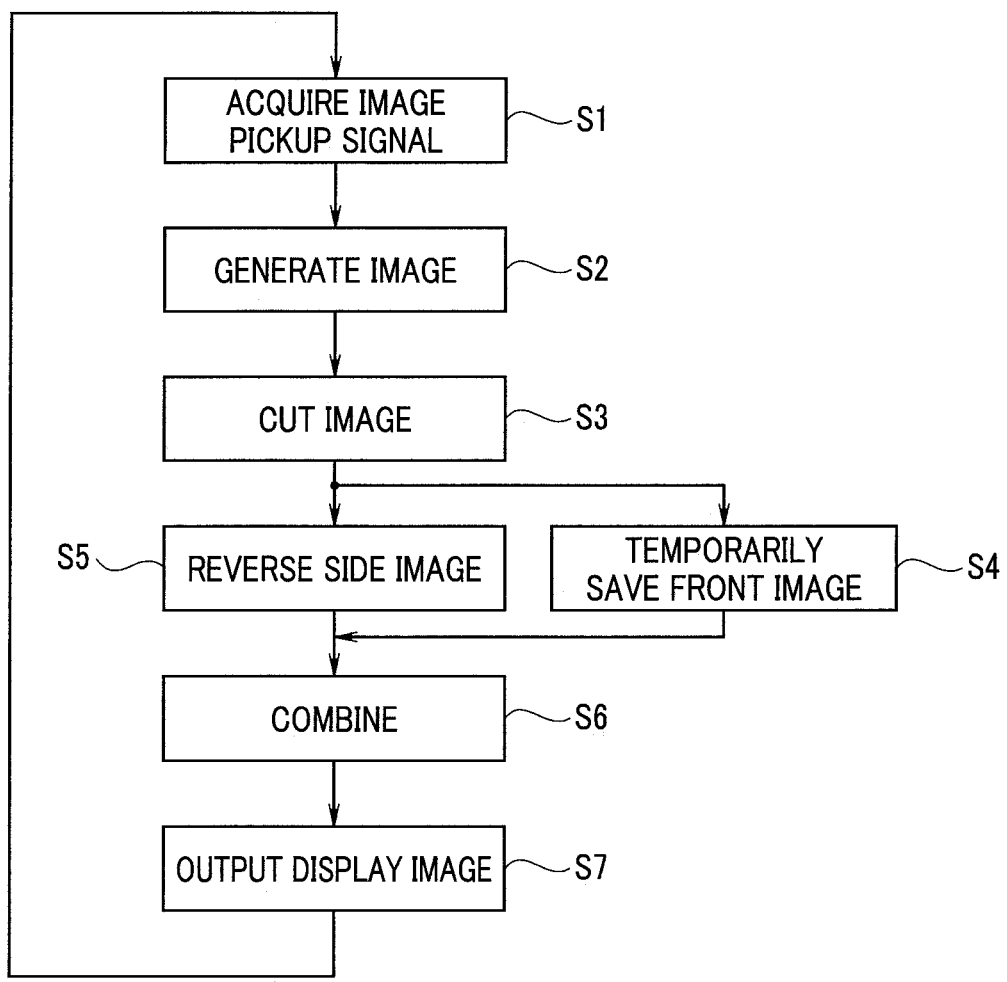
FIG. 5 is a flowchart showing an example of a procedure of a process of displaying the front image and the side image in a control unit of the video processor according to the embodiment of the present invention.

FIG. 5 is a flowchart showing an example of a procedure of a process of displaying the front image FI and the side image SI in the control unit 31 of the video processor 3. The control unit 31 controls the image generation unit 32 to cause the image generation unit 32 to acquire the image pickup signal from the image pickup device 11a (step (hereinafter abbreviated to S) 1).

The control unit 31 then controls the image generation unit 32 to cause the image generation unit 32 to generate the acquired image GI from the image pickup signal (S2) and causes the image processing unit 33 to cut the image (S3). In other words, the image generation unit 32 generates in S2 the acquired image GI from the image pickup signal from the image pickup device 11a, and the image processing unit 33 cuts in S3 the front image FI and the side image SI from predetermined two regions of the acquired image GI, as shown in FIG. 4.

Figure 6:
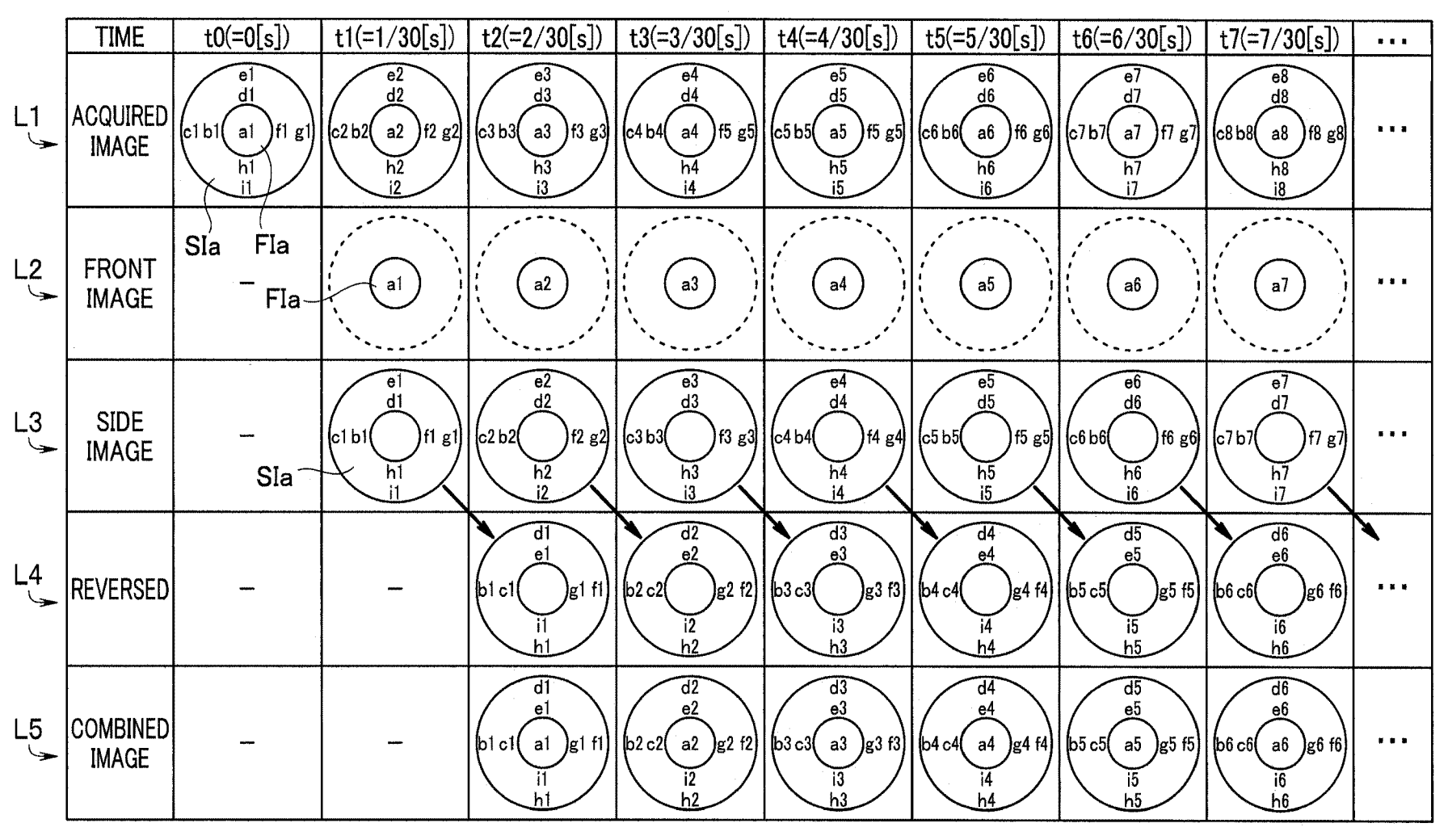

FIG. 6 is a timing chart showing a procedure of image processing performed by the video processor 3.

The horizontal axis of FIG. 6 represents time and shows time passage starting from zero seconds in the form of every 1/30 seconds. The following description will be made of a case where an image is generated every 1/30 seconds from a movie formed of 1/30-second frames and it takes 1/30 seconds to carry out a reversal process that will be described later.

A first row L1 in an upper portion of FIG. 6 shows a front image region FIa and a side image region SIa of the acquired image GI acquired by the image pickup device 11a.

In FIG. 6, a symbol "a1" in the first row L1 at a time point t0 represents one pixel contained in the front image region FIa generated by the image pickup device 11a at the time point t0 (0 [s (second)]). A symbol "a2" in the first row L1 at a time point t1 represents one pixel contained in the front image region FIa generated by the image pickup device 11a at the time point t1 (1/30 [s (second)]). Symbols "a3" to "a8" at other time points t2 to t7 are similarly shown.

Symbols "b1, c1, d1, e1, f1, g1, h1, and i1" in the first row L1 at the time point t0 each represent one pixel contained in the side image region SIa acquired by the image pickup device 11a at the time point t0 (0 [s (second)]). Symbols "b2, c2, d2, e2, f2, g2, h2, and i2" in the first row L1 at the time point t1 each represent one pixel contained in the side image region SIa generated by the image pickup device 11a at the time point t1 (1/30 [s (second)]).

Symbols "b2," "c2," . . . "h8," "i8" at the other points of time t2 to t7 are similarly shown.

The two pixels "b1" and "c1" at the time point t0 are located along a virtual line extending in a radial direction from a center C of the circular front image FI (leftward in FIG. 6). Similarly, the two pixels "d1" and "e1" are located along another virtual line extending in the radial direction from the center C (upward in FIG. 6), the two pixels "f1" and "g1" are located along still another virtual line extending in the radial direction from the center C (rightward in FIG. 6), and the two pixels "h1" and "i1" are located along still another virtual line extending in the radial direction from the center C (downward in FIG. 6).

It is therefore, for example, shown that the pixel b1 is located inward from the pixel c1 in the annular side image region SIa. It is similarly shown that the pixels d1, f1 and h1 are located inward from the pixels e1, g1, and respectively, in the annular side image region SIa. In other words, the pixels c1, e1, g1, and t1 are located outward from the pixels b1, d1, f1, and h1, respectively, in the annular side image region SIa.

Symbols "b2," "c2," and others in the front image region FIa and the side image region SIa that correspond to other rows L2 to L5 at other points of time after the time point t0 are similarly shown.

The second row L2 shows the front image region FIa cut by the image processing unit 33 off the acquired image GI, and the third row L3 shows the side image region SIa cut by the image processing unit 33 off the acquired image GI.

Therefore, the first row L1 shows the front image region FIa and the side image region SIa before cut by the image processing unit 33, and the second row L2 and the third row L3 show the front image region FIa and the side image region SIa after cut by the image processing unit 33.

The front image FI containing the pixel a1 and the side image SI containing the pixels b1 to i1 are cut at the time point t1 (1/30 [s]) off the acquired image GI at the time point t0 (0 [s (second)]).

Referring back to FIG. 5, after S3, the control unit 31 controls the image processing unit 33 to temporarily save data on the front image FI in the memory 33a (S4) and reverse the side image SI (S5).

The reversal process is a process of reversing the order of the positions of the pixels arranged in the radial direction from a predetermined position (center C of front image region FI in the description), that is, a reversing process, i.e., the process of turning the pixels inside out in the radial direction.

Figure 7:
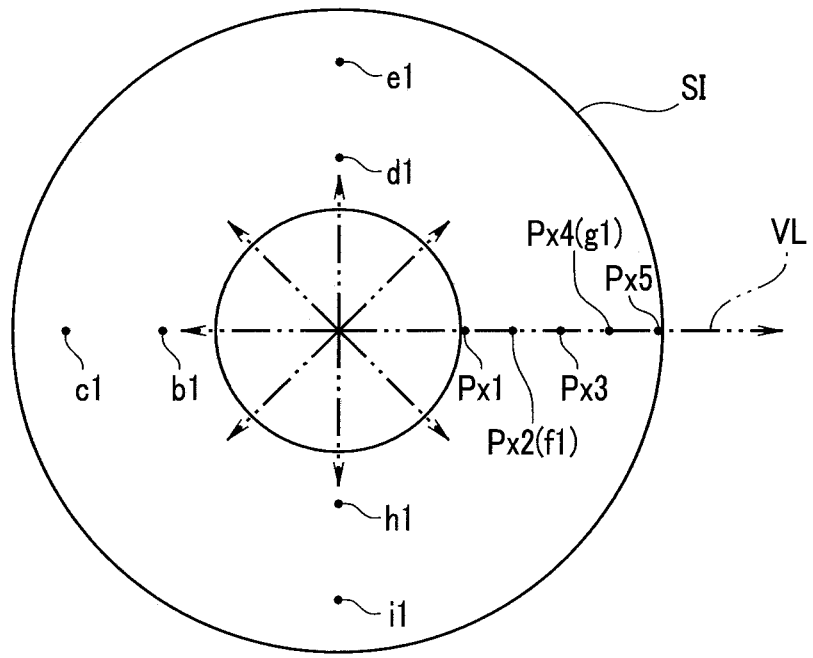
FIG. 7 describes pixel positions before a reversal process according to the embodiment of the present invention.
Figure 8:
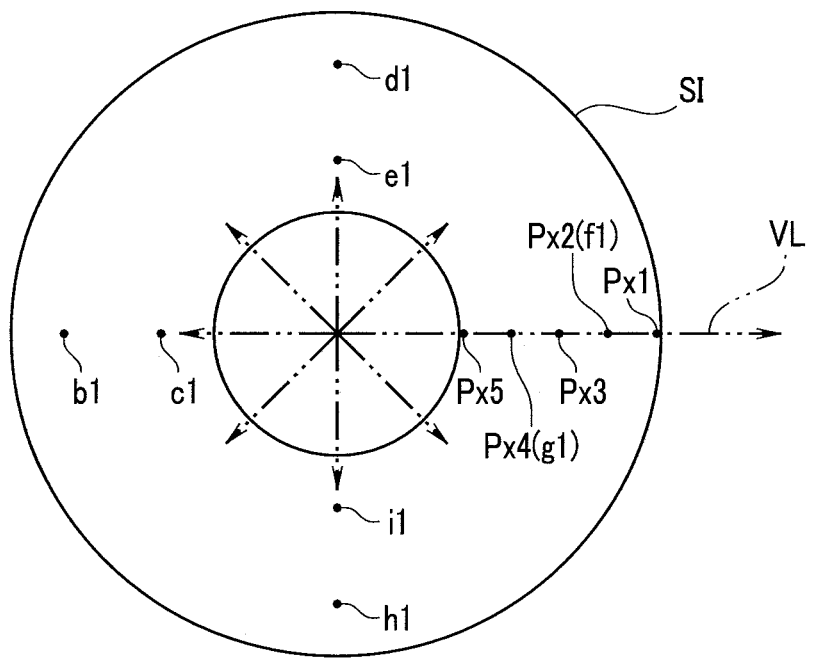
FIG. 8 describes the pixel positions after the reversal process according to the embodiment of the present invention.

FIGS. 7 and 8 describe the reversal process. FIG. 7 describes the pixel positions before the reversal process. FIG. 8 describes the pixel positions after the reversal process. FIG. 7 shows the annular side image SI. The side image SI has an annular shape around the center C. The center C coincides with the center of the circular front image FI.

The reversal process is a process of rearranging the order of the pixels in the side image SI that are arranged from the inner side toward the outer side of the annular image to the order of the pixels arranged from the outer side to the inner side. Specifically, a plurality of pixels are located on a virtual line VL radially extending from the center C in the outer circumferential direction, as shown in FIG. 7. FIG. 7 shows pixels Px5 to Px5 at five points on the virtual line VL for ease of the description.

The reversal process is a process of changing the arrangement of the pixels arranged from the center C in the outer circumferential direction to the arrangement of the pixels arranged from the outer side of the side image SI toward the center C. FIG. 8 shows the pixels Px1 to Px5 at five points after the rearrangement of the pixels in FIG. 7 in the reversal process. In FIG. 8, the pixel Px1 located on the innermost side in the annular shape before the reversal process is disposed on the outermost side in the annular shape, and the pixel Px5 located on the outermost side in the annular shape before the reversal process is disposed on the innermost side in the annular shape. In other words, on the virtual line VL in FIG. 8, the five pixels Px1, Px2, Px3, Px4, and Px5 arranged in the presented order from the center C in the outer circumferential direction are rearranged to the order of Px5, Px4, Px3, Px2, and Px1.

The pixels on the virtual line are determined, for example, by pixel interpolation and caused to undergo the reversal process, and the reversed pixels are determined in terms of the pixel value in each of the pixel position, for example, by the pixel interpolation again.

Assuming that the pixel f1 in the acquired image GI in the first row L1 in FIG. 6 described above is the pixel Px2 in FIG. 7, and that the pixel g1 in FIG. 6 is the pixel Px4, the pixel f1 located on the inner side of the pixel g1 in FIG. 7 is disposed on the outer side of the pixel g1 in FIG. 8. The arrangement of the other pixels b1, c1, d1, e1, h1, and i1 is also changed as shown in FIG. 8, as in the case of the pixels f1 and g1.

As described above, the reversal process is a process of changing the order of a plurality of pixels arranged from a predetermined position in the radial direction in such a way that the position of a pixel disposed on an inner circumferential side of the annular side image SI is swapped for the position of a pixel disposed on an outer circumferential side of the annular side image SI.

Briefly, the reversal process is a process of changing the pixel positions in such a way that a pixel closer to the center of the side image SI (on inner side) is changed to a pixel closer to the outer side of the annular shape and a pixel closer to the outer side of the side image SI is changed to a pixel closer to the center (on inner side).

The pixel positions are changed in the reversal process, for example, by conversion, such as polar coordinate conversion, around the center C as an origin. In other words, the processor 31a swaps the position of a pixel disposed on the inner circumferential side of the side image SI for the position of a pixel disposed on the outer circumferential side of the side image SI based on polar coordinates with respect to a predetermined position, for example, the center C of an image to be displayed on the display apparatus 4.

Figure 9:
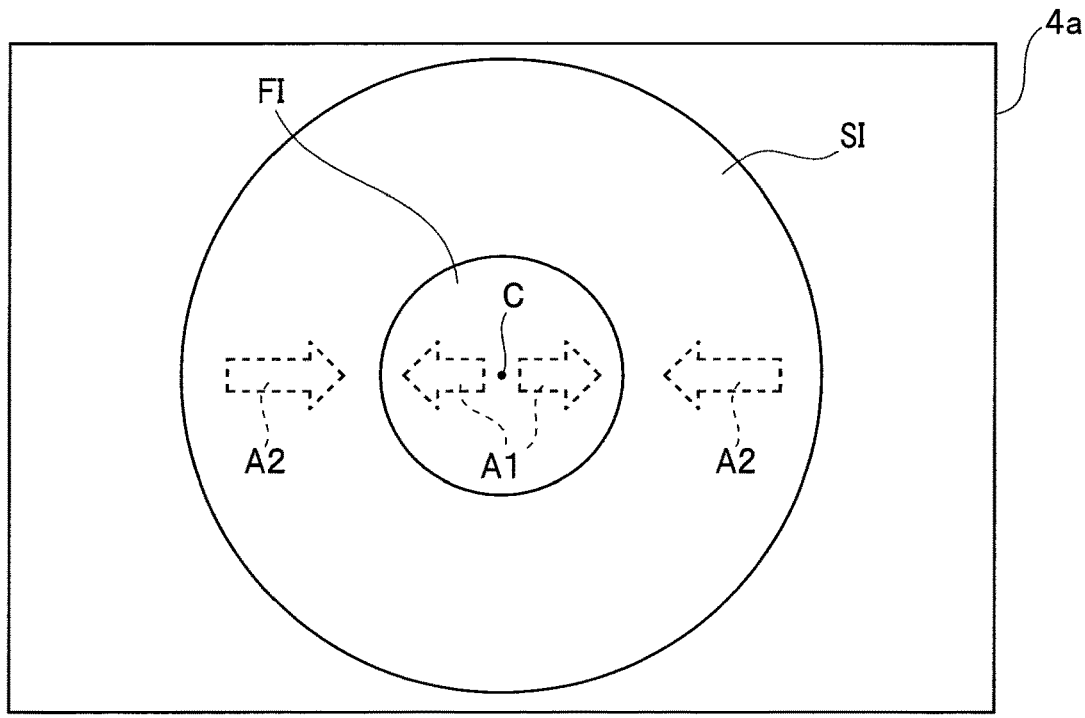
FIG. 9 describes motions of the front image and the side image in a case where the reversal process according to the embodiment of the present invention is not carried out.

FIG. 9 describes motions of the front image and the side image in a case where no reversal process is carried out. FIG. 9 shows an example of the front image FI and the side image SI displayed on the display screen 4a of the display apparatus 4.

When no reversal process is carried out, and the insertion section 5 of the endoscope 2 is moved in the subject, the front image and the side image move in different directions. For example, in large intestine endoscopy, the distal end section 11 of the insertion section 5 is first inserted to a deep position in the subject and then gradually pulled back to perform screening, which is examination of evaluating whether or not a diseased site is present.

Light incident via the side observation window W2 is reflected once off the mirror shown in FIG. 2 and brought into focus on the image pickup surface of the image pickup device 11a. For example, when the insertion section 5 advances to a deep position in the subject, the side image SI generated by an optical image formed by the light reflected once off the mirror moves as shown in FIG. 9.

When the insertion section 5 advances to the deep position in a lumen of the subject, an inner wall of the front image FI moves from the center C in the outer circumferential direction. In other words, when the insertion section 5 advances to the deep position in the lumen of the subject, the front image FI changes in such a way that an inner wall image moves in directions labeled with dotted-line arrows A1.

On the other hand, when the insertion section 5 advances to the deep position in the lumen of the subject, the inner wall of the annular side image SI moves from the outer side toward the center C, as shown in FIG. 9. In other words, when the insertion section 5 advances to the deep position in the lumen of the subject, the side image SI changes in such a way that the inner wall image moves in directions labeled with dotted-line arrows A2. In this process, the arrows A1 and A2 are oriented in opposite directions.

The motion of the front image FI and the motion of the side image SI are therefore reversed, and it is therefore difficult for a surgeon or the like to intuitively understand, for example, the position of a diseased site.

In contrast, the aforementioned reversal process that the side image SI is caused to undergo eliminates the difficulty in intuitive understanding of, for example, the position of a diseased site.

Figure 10:
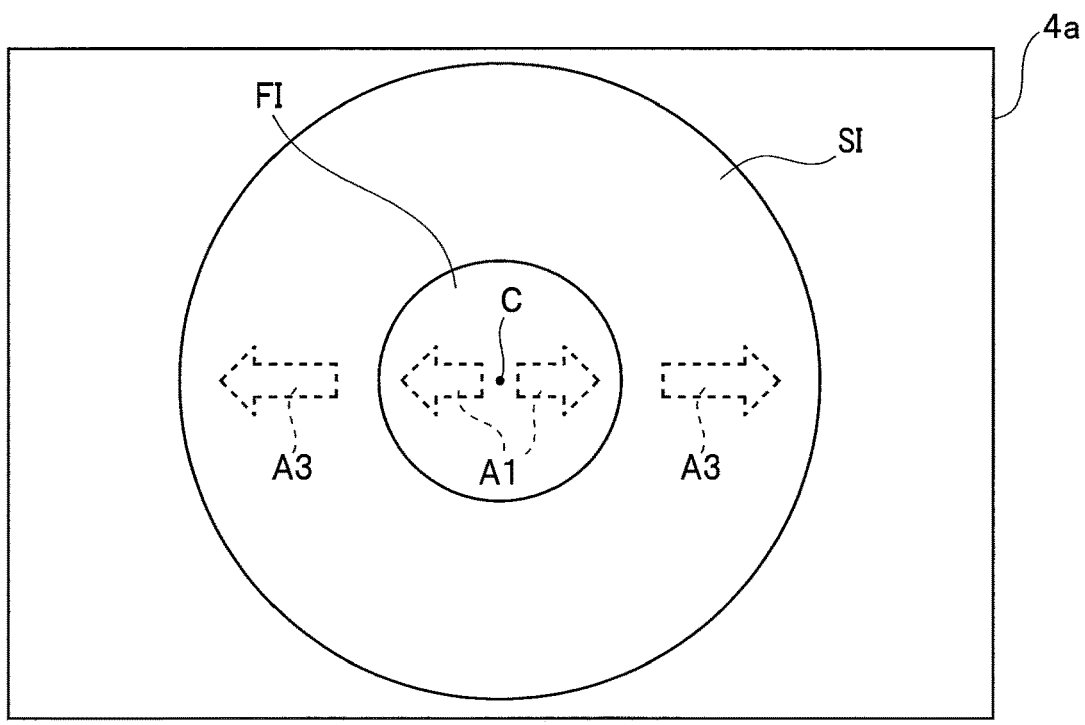
FIG. 10 describes the motions of the front image and the side image in a case where the reversal process according to the embodiment of the present invention is carried out.

FIG. 10 describes the motions of the front image and the side image in a case where the reversal process is carried out. FIG. 10 shows an example of the front image FI and the side image SI displayed on the display screen 4a of the display apparatus 4.

For example, when the insertion section 5 advances to the deep position in the lumen of the subject, the front image FI changes in such a way that the inner wall of the front image FI moves from the center C in the outer circumferential direction, and the side image SI also changes in such a way, that the inner wall of the side image SI also moves from the center C in the outer circumferential direction, as shown in FIG. 10. In other words, when the insertion section 5 advances to the deep position in the lumen of the subject, movement directions (A1) of the inner wall of the front image FI are the same as the movement directions (A3) of the inner wall of the side image SI.

Therefore, when the side image SI generated by the optical image formed by the light reflected once off the mirror section 11b3 undergoes the reversal process described above, the front image FI and the side image SI having undergone the reversal process (hereinafter also referred to as reversed side image SIv) move in the same direction, whereby a surgeon or the like readily intuitively understands, for example, the position of a diseased site.

To this end, the side image SI is caused to undergo the reversal process in S5 in FIG. 5.

Referring back to FIG. 5, the control unit 31 carries out a combination process of combining the front image FI with the side image SI (S6).

In FIG. 6, the side image SI at the time point t1 (1/30 [s]) is caused to undergo the reversal process, and the reversed side image SIv is generated at the time point t2 (2/30 [s]) in a fourth row L4. At the time point t2 (2/30[s]), the front image FI at the time point t1 is combined with the reversed side image SIv acquired at the time point t2 to generate a combined image.

The generated combined image is an image that is a combination of the front image FI and the reversed image of the side image SI generated at the same timing as the time point t0 (0 (0 [s (seconds)]).

Similarly, a subject image acquired at the time point t1 (1/30 [s]) is also processed in the same manner in which a subject image acquired at the time point t0 (0 [s]) is processed. In other words, the front image FI and the side image SI are cut and acquired at the time point t2, the reversed side image SIv is acquired at the time point t3 (3/30 [s]), the front image FI is combined with the reversed side image SIv, and an image signal representing the combined image is outputted to the display apparatus 4. Similarly, the control unit 31 causes the following images, the front image FI and the side image SI, acquired at each time point to undergo the processes in S2 to S7.

In FIG. 6, a process of reversing the side image SI and a process of combining the front image FI with the side image SI having been reversed are carried out within 1/30 [s]. However, when it takes about 1/30 [s] to carry out the process of combining the front image FI with the side image SI having been reversed, the timing at which the combined image is generated is set to be delayed by another 1/30 [s] from the timing at which the side image is reversed.

As described above, the processor 31a of the control unit 31 causes a subject image, which is the side image SI captured with the image pickup device 11a, to undergo the reversal process of reversing the order of a plurality of pixels arranged from a predetermined position in the radial direction, generates a combined image that is the combination of the front image FI and the reversed side image SIv, which is the side image SI having undergone the reversal process, and causes the display apparatus 4 to display the combined image as the display image.

In particular, the processor 31a adjusts a timing at which at least the front image FI is displayed in such a way that the front image FI acquired simultaneously with the side image SI is displayed at a timing that accords with a timing at which the reversed side image SIv having undergone the reversal process is displayed on the display apparatus 4. In this process, the processor 31a adjusts the timing at which the front image FI is displayed to cause the display apparatus 4 to display at the same timing the reversed side image SIv and the front image FI acquired simultaneously with the side image SI.

As described above, the front image FI and the side image SI caused to undergo the reversal process described above and displayed on the display screen 4a of the display apparatus 4 not only cause no difficulty in a surgeon or the like's intuitive understanding of the position of a diseased site but cause the surgeon or the like to have no odd feeling due to a discrepancy between display timings of the two images because the timings at which the two images are displayed are adjusted.

The embodiment described above can therefore provide an endoscope apparatus, an endoscopic image processing apparatus, and a method for operating the endoscopic image processing apparatus that allow the timings at which a front image, a side image, and other images are displayed on the display apparatus to coincide with one another and therefore cause a person who views the two images to have no odd feeling.

Modifications of the embodiment described above will next be described.

Modification 1

In the endoscope apparatus according to the embodiment described above, the display timing of the front image FI always accords with the display timing of the reversed side image SIv. Instead, the display timing of the front image FI may accord with the display timing of the reversed side image SIv only as required.

For example, assuming that the endoscope apparatus 1 has two modes, a process of causing the display timings of the two images to coincide with each other is carried out when a first mode is selected, as in the embodiment described above, whereas the process of causing the display timings of the two images to coincide with each other is not carried out when a second mode is selected.

For example, in a large intestine examination, a surgeon first inserts the distal end section 11 of the insertion section 5 to a deep position in the large intestine and then pulls the insertion section 5 back for examination of whether or not a diseased site is present. Therefore, at the first insertion of the insertion section 5, the operator only views the front image FI but does not view the side image SI. In such a case, the display timing of the front image FI does not necessarily accord with the display timing of the reversed side mage SIv, so that it is desirable in some cases to reduce the load on the image processing unit 33 so that the front image FI is quickly displayed.

For example, the user can operate the operation panel 3a to select a desired mode from the two modes. The image processing unit 33 does not carry out the process of causing the display timing of the front image FI and the display timing of the reversed side image SIv to coincide with each other when the second mode is set.

In other words, when generating a combined image in S8 in FIG. 5, the image processing unit 33 uses a latest front image FI to generate the combined image that is the combination of the front image FI and the reversed side image SIv.

Figure 11:
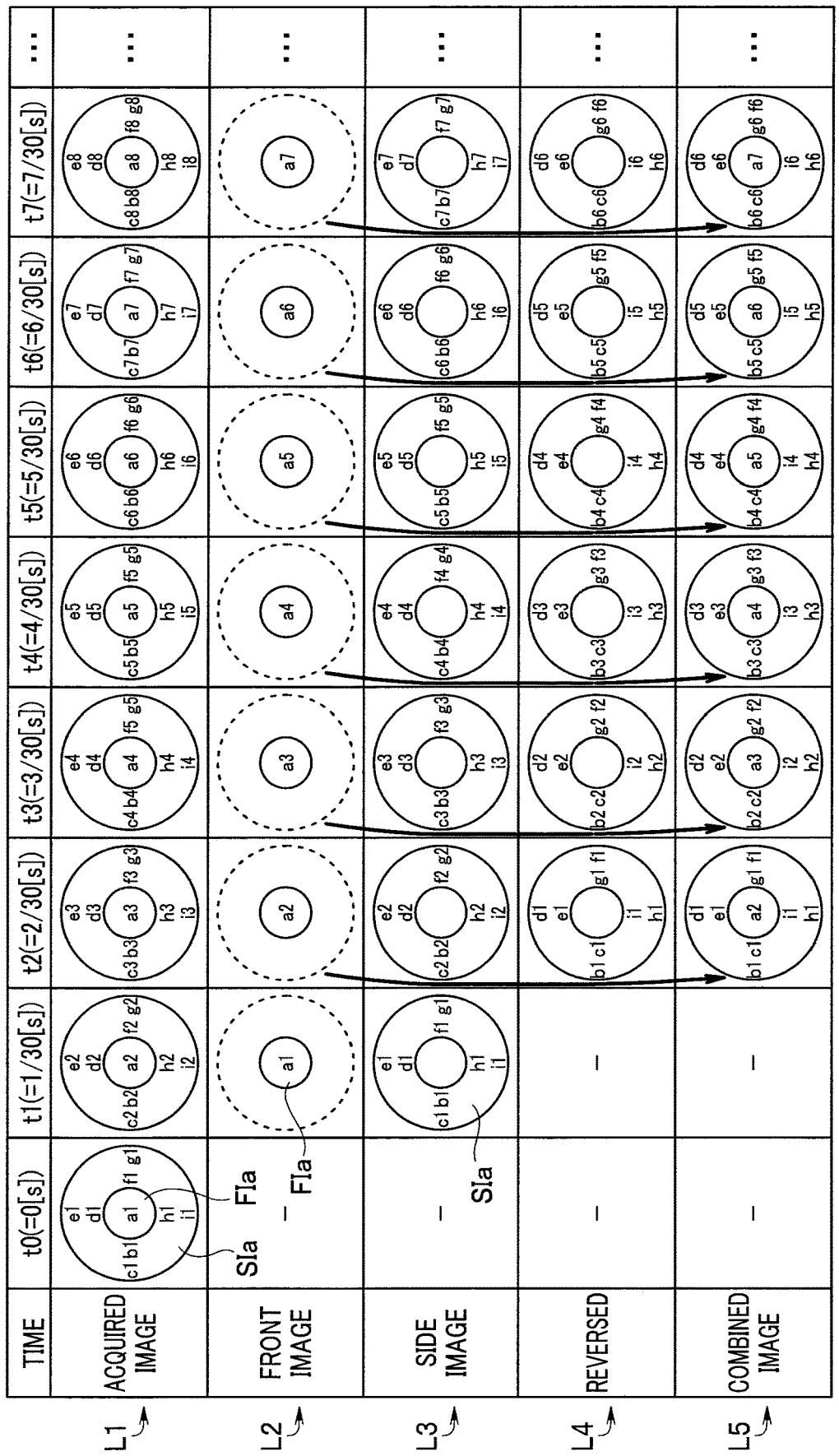
FIG. 11 is a timing chart showing a procedure of image processing performed by the video processor according to Modification 1 of the embodiment of the present invention.

FIG. 11 is a timing chart showing a procedure of image processing performed by the video processor 3 according to the present modification. The horizontal axis of FIG. 11 represents time and shows time passage starting from zero seconds in the form of every 1/30 seconds, as in FIG. 6 shown above.

As shown in a fifth row L5, at the time point t2 (2/30 [s]), the front image FI acquired at the time point t1 is combined with the reversed side image SIv at the time point t2. The front image FI is therefore a latest front image, and the side image SI is an image acquired and reversed at a preceding time point.

In other words, out of the front image FI and the side image SI acquired at the time point t1, the front image FI is displayed at a timing before the side image SI acquired at the time point t1 has not yet been reversed.

Images acquired at other time points in the first row L1 are also caused to undergo image processing, as shown in FIG. 11. For example, a surgeon or the like switches the mode to the second mode at the first insertion of the insertion section 5 to allow the front image FI to be displayed in a real-time manner.

As described above, the endoscope apparatus 1 has the first mode and the second mode, and the processor 31a adjusts the display timings in the first mode in such a way that the front image FI is displayed at the timing at which the side image SI is displayed but does not perform the timing adjustment in the second mode.

Therefore, according to the present modification, the user can select whether or not the display timings of the front image FI and the side image SI coincide with each other.

In FIG. 11, the process of reversing the side image SI and the process of combining the front image FI with the side image SI having been reversed are carried out within $\frac{1}{30}$ [s]. However, when it takes about $\frac{1}{30}$ [s] to carry out the process of combining the front image FI with the side image SI having been reversed, the timing at which the combined image is generated is set to be delayed by another $\frac{1}{30}$ [s] from the timing at which the side image SI is reversed.

Modification 2

In Modification 1 described above, the user, who is a surgeon or the like, can change the mode, that is, can set the mode in such a way that the display timing of the front image FI coincides or does not coincide with the display timing of the reversed side image SIv. Instead, the two modes may be automatically switched from one to the other.

In the present modification, the image processing unit 33 calculates a motion vector of a predetermined region of the side image SI and switches the display mode to a display mode in which the display timing of the front image FI coincides with the display timing of the reversed side image SIv only when the calculated motion vector has a size greater than or equal to a predetermined threshold.

When the distal end section 11 is not in motion, the surgeon or the like has no odd feeling even when the display timing of the front image FI does not coincide with the display timing of the side image SI. However, for example, when the large intestine suddenly moves, the surgeon or the like has an odd feeling when the display timing of the front image FI deviates from the display timing of the reversed side image SIv. Therefore, in such a case, the display timing of the front image FI is caused to accord with the display timing of the reversed side image Siv when the motion vector of the side image SI has a size greater than or equal to the predetermined threshold, whereby the surgeon or the like has no odd feeling.

In other words, the processor 31a detects the motion vector of the side image SI, compares an absolute value of the motion vector with the predetermined threshold, and selects the first mode when the absolute value of the motion vector is greater than or equal to the predetermined threshold.

Therefore, according to the present modification, in which whether or not the display timing of the front image FI coincides with the display timing of the side image SI can be automatically selected, the load on the image processing unit 33 increases only temporarily but is rather reduced in consideration of the overall process carried out by the image processing unit 33.

In the example described above, the motion vector is detected in the side image SI but may instead be calculated in at least one of the front image FI and the side image SI.

Modification 3

In the embodiment and the modifications described above, one annular side image is revered. Instead, the side image may be cut into a plurality of side images in the radial direction to divide the side image into a plurality of regions in the circumferential direction, and the divided regions may be reversed.

Figure 12:
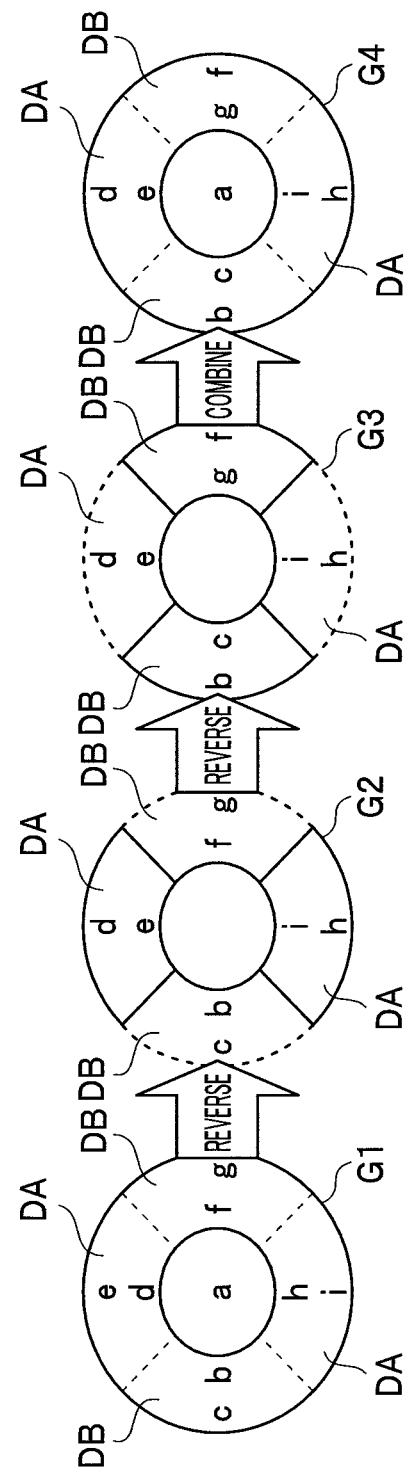
FIG. 12 describes the reversal process that divided regions are caused to undergo according to Modification 3 of the embodiment of the present invention.

FIG. 12 describes the reversal process that the divided regions are caused to undergo. In FIG. 12, an image G1 represents the front image FI and the side image SI of the acquired image GI.

The side image SI of the image G1 is cut into four images along four dotted lines extending from the center C of the front image FI in the outer circumferential direction. As a result, the annular side image SI is divided into four images in the circumferential direction. The four regions are formed of two upper and lower divided regions DA and two right and left divided regions DB.

A process of reversing the two divided regions DA and a process of reversing the two divided regions DB are carried out for each divided region. The process of reversing the two divided regions DA is first carried out, and after the process of reversing the two divided regions DA, the process of reversing the two divided regions DB is carried out.

Figure 13:
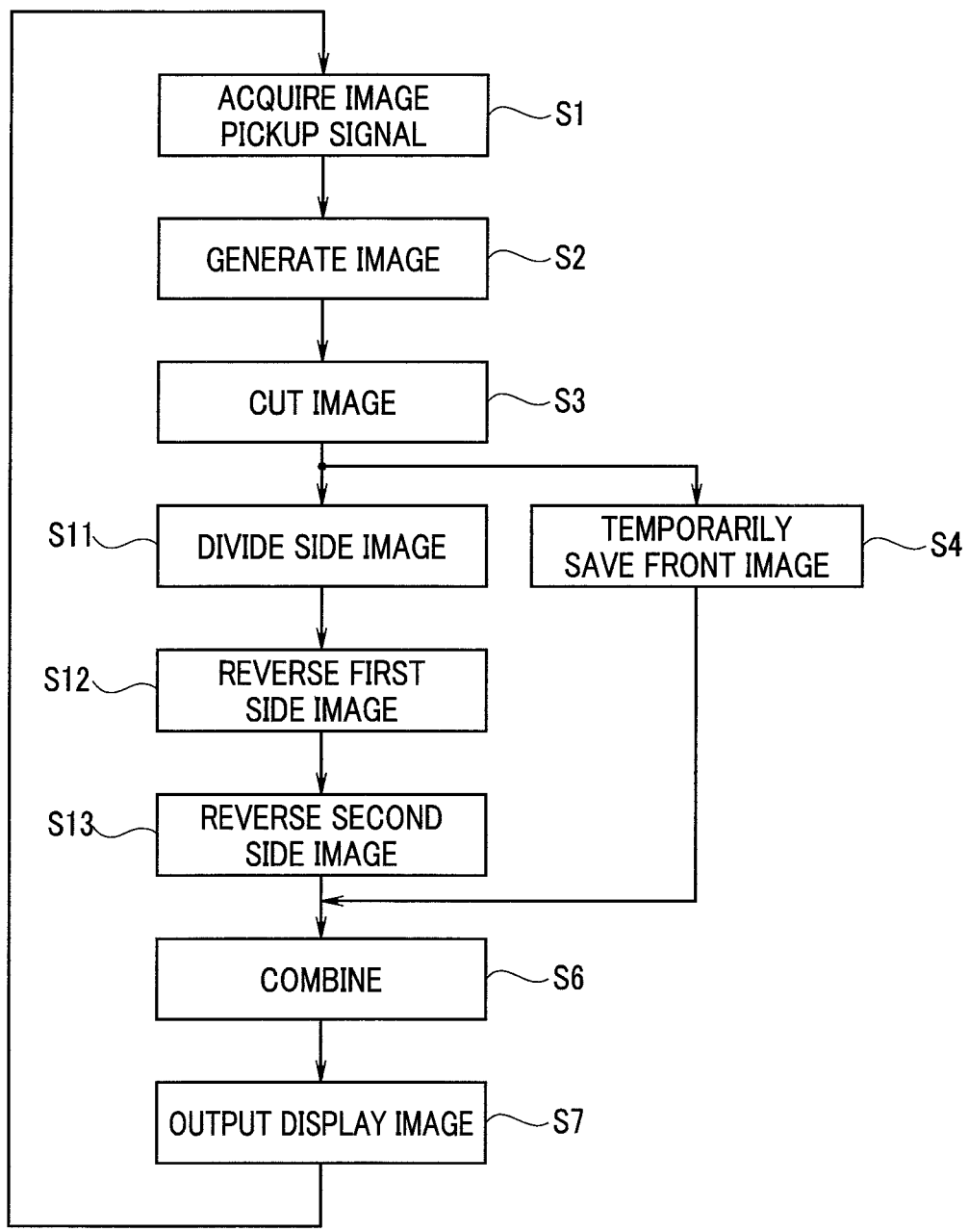
FIG. 13 is a flowchart showing an example of the procedure of the process of displaying the front image and the side image in the control unit of the video processor according to Modification 3 of the embodiment of the present invention.

FIG. 13 is a flowchart showing an example of the procedure of the process of displaying the front image FI and the side image SI in the control unit 31 of the video processor 3 in Modification 3. In FIG. 13, the same processes as the processes in FIG. 5 have the same step numbers and will not be described.

The image processing unit 33 carries out the image cutting process in S3 and then divides the side image SI (S11), as shown in FIG. 13.

The image processing unit 33 then reverse a first side image (S12). In S12, the two divided regions DA described above are reversed. In FIG. 12, a side image G2 represents an image after the process in S12.

After S12, the image processing unit 33 reverses a second side image (S13). In S13, the two divided regions DB described above are reversed. In FIG. 12, a side image G3 represents an image after the process in S13.

After S13, the image processing unit 33 combines the front image FI temporarily saved in the memory 33a in S4 with the side image SI formed of the four reversed divided regions DA and DB (S6). In FIG. 12, an image G4 is an image formed in S6.

Figure 14:
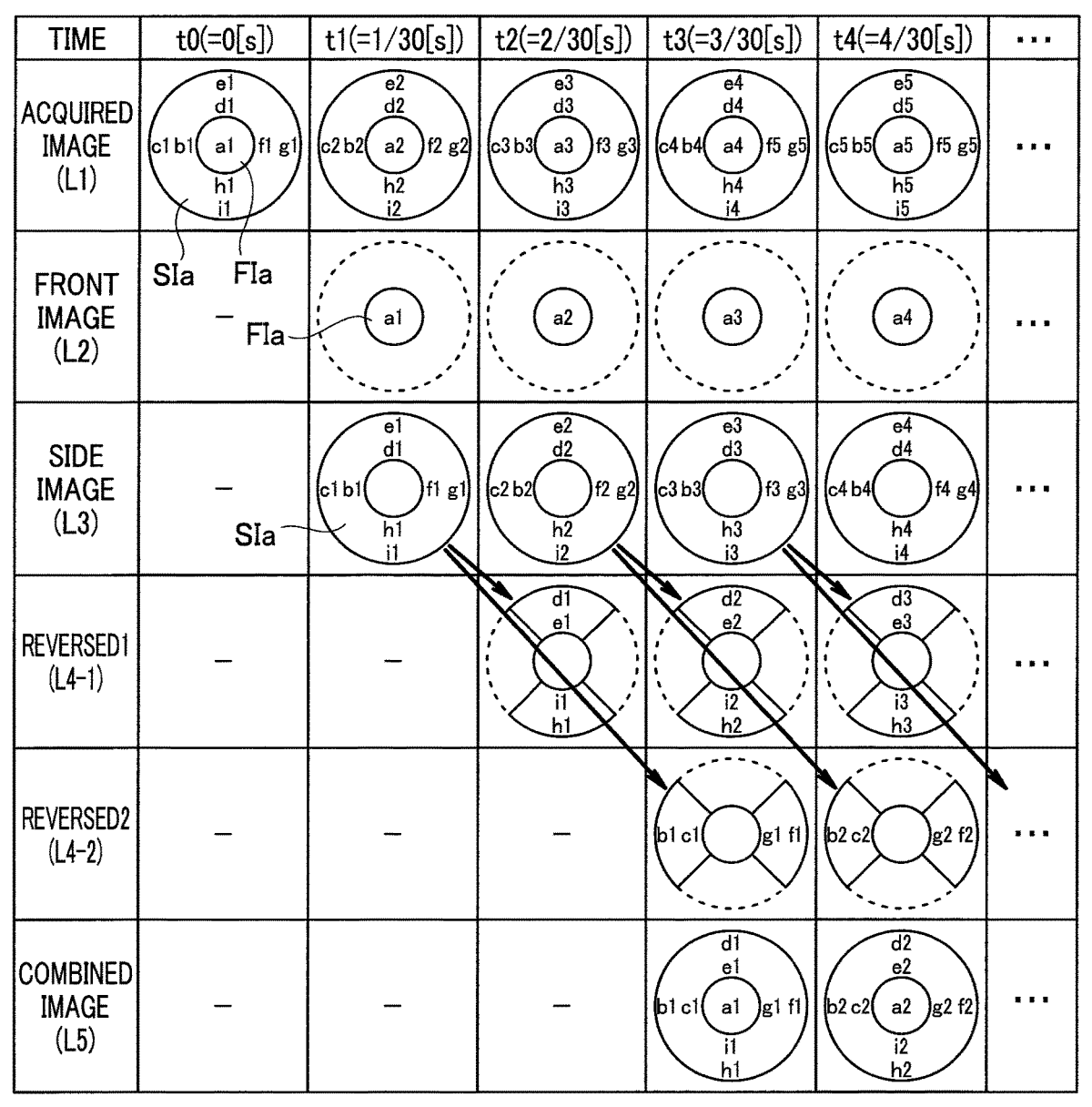

FIG. 14 is a timing chart showing a procedure of image processing performed by the video processor 3 according to the present modification. The horizontal axis of FIG. 14 represents time and shows time passage starting from zero seconds in the form of every $\frac{1}{30}$ seconds, as in FIG. 6 shown above.

In a fourth row L4-1, the two upper and lower divided regions DA are reversed. In a fourth row L4-2, the two right and left divided regions DB are reversed.

In the present modification, the front image FI is combined with the side image SI having been reversed at the time point t3 ($\frac{3}{30}$ [s]), as shown in a fifth row L5. Images acquired at other time points in the first row L1 are also processed, as shown in FIG. 14.

As described above, dividing the side image SI into two portions allows a process target region in one reversal process carried out by the image processing unit 33 to be halved, whereby the load in one reversal process is reduced. Dividing the side image SI therefore provides an advantage of no necessity of an increase in processing performance of the image processing unit 33.

In the example described above, the side image SI is divided into four, and the reversal process is carried out on every two divided regions. The number of divided side images SI may be two or more, and further, the number of reversal processes to be carried out may be three or more.

Further, in the example described above, the side image SI is divided into a plurality of images in the circumferential direction and may instead be cut in the circumferential direction to divide the side image SI into a plurality of images in the radial direction.

In FIG. 14, the process of reversing the side image SI and the process of combining the front image FI with the side image SI having been reversed are carried out within 1/30[s]. However, when it takes about 1/30 [s] to carry out the process of combining the front image FI with the side image SI having been reversed, the timing at which the combined image is generated is set to be delayed by another 1/30 [s] from the timing at which the side image SI is reversed.

Figure 15:
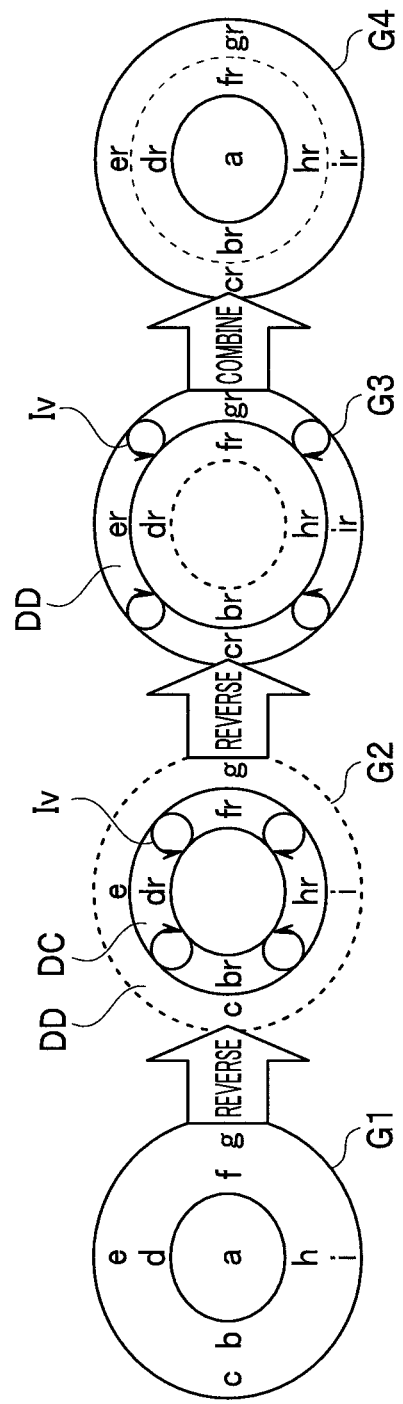
FIG. 15 describes the reversal process that regions divided in a radial direction are caused to undergo according to Modification 3 of the embodiment of the present invention.

FIG. 15 describes the reversal process that the regions divided in the radial direction are caused to undergo. The side image SI of the image G1 is divided into two in the radial direction from the center C of the front image FI, as shown in FIG. 15.

In FIG. 15, an inner divided region DC is caused to undergo the reversal process, as shown in G2. In FIG. 15. In FIG. 15, circular arrows Iv represent that the reversal process is carried out, and the reversed pixels are labeled with br, dr, fr, and hr.

After the divided region DC is reversed, an outer divided region DD is reversed, as shown by G3. The image processing unit 33 combines the front image FI temporarily saved in the memory 33a in S4 with the side image SI formed of the two reversed divided regions DC and DD, and the combined image labeled with G4 is displayed.

Further, the side image SI is divided into two in the radial direction and may instead be divided into three or more in the radial direction.

As described above, in the present modification, the processor 31a divides an acquired side image SI into a plurality of portions and carries out the reversal process for each divided portion. In particular, the processor 31a reverses the plurality of portions of the side image SI that are divided in the circumferential or radial direction in a predetermined order along a temporal axis.

Modification 4

In Modification 3 described above, a side image is divided, and a side image may be automatically divided.

For example, a motion vector of a side image is calculated. When the size of the motion vector is smaller than a predetermined value, the side image SI is not divided, and the reversal process described above is carried out, whereas when the size of the motion vector is greater than or equal to the predetermined value, the side image is divided, and the divided regions are caused to undergo the reversal process.

In an image compression technology, such as MPEG, when the size of the motion vector is small, an image in a preceding frame is used at a high usage rate in motion compensation, so that the load in the compression process is small, whereby the load on the image processing unit 33 does not increase even when the entire side image is caused to undergo the reversal process.

In contrast, when the size of the motion vector is large, an image in a preceding frame is used at a low usage rate in the motion compensation, so that the load in the compression process is large, and the reversal process on the divided side images increases the load on the image processing unit 33. The motion vector may be detected in the front image FI.

The processor 31a may therefore detect the motion vector of at least one of the acquired front image FI and side image SI, compare an absolute value of the motion vector with a predetermined threshold, and switch between whether to divide the side image SI into a plurality of portions to cause the divided portions to undergo the reversal process or to carry out the reversal process without dividing the side image SI into a plurality of portions.

When the size of the motion vector is greater than or equal to the predetermined threshold, the side image SI is not divided.

As described above, the embodiment and the modifications described above can provide an endoscope apparatus, an endoscopic image processing apparatus, and a method for operating the endoscopic image processing apparatus that allow the timings at which a front image and a side image are displayed on the display apparatus to coincide with each other and therefore cause a person who views the two images to have no odd feeling.

The present invention is not limited to the embodiment described above, and a variety of changes, improvements, and other modifications can be made to the extent that the changes, improvements, and other modifications do not change the gist of the present invention.

What is claimed is:
1. An endoscope apparatus comprising:
an insertion section configured to be inserted into a subject;
a first optical system configured to acquire an image of a first subject in front of the insertion section;
a second optical system configured to reflect an odd number of times an image of a second subject in a lateral direction of the insertion section and acquire the reflected second subject image;
an image pickup device configured to pick up the first subject image and the second subject image acquired by the first optical system and the second optical system; and
a processor configured to carry out a reversal process on the second subject image picked up with the image pickup device, the reversal process reversing an order of a plurality of pixels located in the second subject image and arranged from a predetermined position in a radial direction, and cause a display apparatus to display the first subject image and the second subject image having undergone the reversal process as a display image,
wherein the processor is configured to adjust a timing at which at least the first subject image is displayed in such a way that the first subject image acquired simultaneously with the second subject image is displayed at a timing that accords with a timing at which the second subject image having undergone the reversal process is displayed on the display apparatus.
2. The endoscope apparatus according to claim 1, wherein the processor adjusts the timing at which the first subject image is displayed to cause the display apparatus to display at a same timing the second subject image having undergone the reversal process and the first subject image acquired simultaneously with the second subject image.

3. The endoscope apparatus according to claim 1, wherein the reversal process is a changing process of changing the order of the plurality of pixels arranged from the predetermined position in the radial direction in such a way that a first position of a first pixel disposed on an inner circumferential side of the second subject image is swapped for a second position of a second pixel disposed on an outer circumferential side of the second subject image.

4. The endoscope apparatus according to claim 3, wherein the processor performs the changing process based on polar coordinates with respect to the predetermined position of an image to be displayed on the display apparatus.

5. The endoscope apparatus according to claim 1, wherein the number of odd times is one.

6. The endoscope apparatus according to claim 1,
wherein the endoscope apparatus has a first mode and a second mode switchable from one to another, and
the processor is configured to adjust the timing in the first mode and not to adjust the timing in the second mode.

7. The endoscope apparatus according to claim 6, wherein the processor is configured detect a motion vector of at least one of the first subject image and the second subject image, compare an absolute value of the motion vector with a predetermined threshold, and select the first mode when the absolute value of the motion vector is greater than or equal to the predetermined threshold.

8. The endoscope apparatus according to claim 1, wherein the processor divides the acquired second subject image into a plurality of portions and carries out the reversal process for each divided portion.

9. The endoscope apparatus according to claim 8, wherein the processor reverses the plurality of portions of the second subject image that are divided in a circumferential or radial direction in a predetermined order along a temporal axis.

10. The endoscope apparatus according to claim 8, wherein the first subject image and the second subject image in which the plurality of portions have undergone the reversal process are displayed on the display apparatus at a same timing.

11. The endoscope apparatus according to claim 1, wherein the processor detects a motion vector of at least one of the acquired first subject image and the acquired second subject image, compares an absolute value of the motion vector with a predetermined threshold, and switches between whether to divide the second subject image into a plurality of portions to cause the divided portions to undergo the reversal process, or to carry out the reversal process without dividing the second subject image into a plurality of portions.

12. The endoscope apparatus according to claim 1, wherein the second subject image has an annular shape or a partially annular shape.

13. An endoscopic image processing apparatus configured to be connected to an endoscope including an insertion section, a first optical system configured to acquire an image of a first subject in front of the insertion section, a second optical system configured to reflect an odd number of times an image of a second subject in a lateral direction of the insertion section and acquire the reflected second subject image, and an image pickup device configured to pick up the first subject image and the second subject image acquired by the first optical system and the second optical system, the endoscopic image processing apparatus comprising:
a processor including hardware,
wherein the processor carries out a reversal process on the second subject image picked up with the image pickup device, the reversal process reversing an order of a plurality of pixels located in the second subject image and arranged from a predetermined position in a radial direction, and outputs an image signal that causes a display apparatus to display the first subject image and the second subject image having undergone the reversal process as a display image, and
the processor adjusts a timing at which at least the first subject image is displayed in such a way that the first subject image acquired simultaneously with the second subject image is displayed at a timing that accords with a timing at which the second subject image having undergone the reversal process is displayed on the display apparatus.

14. A method for operating an endoscopic image processing apparatus including a processor and connected to an endoscope including a first optical system configured to acquire a first subject image, a second optical system configured to reflect an odd number of times a second subject image in a lateral direction of the first subject image and acquire the reflected second subject image, and an image pickup device configured to pick up the first subject image and the second subject image,
wherein the processor carries out a reversal process on the second subject image, the reversal process reversing an order of a plurality of pixels located in the second subject image and arranged from a predetermined position in a radial direction, and outputs an image signal that causes a display apparatus to display the first subject image and the second subject image having undergone the reversal process as a display image, and
the processor adjusts a timing at which at least the first subject image is displayed in such a way that the first subject image acquired simultaneously with the second subject image is displayed at a timing that accords with a timing at which the second subject image having undergone the reversal process is displayed on the display apparatus.

* * * * *